United States Patent
Kopperschmidt et al.

(10) Patent No.: US 10,569,001 B2
(45) Date of Patent: Feb. 25, 2020

(54) DEVICE AND METHOD FOR DETERMINING AN OPTIMUM DIALYSATE FLOW FOR AN EXTRACORPOREAL BLOOD TREATMENT WITH AN EXTRACORPOREAL BLOOD TREATMENT DEVICE

(71) Applicant: FRESENIUS MEDICAL CARE DEUTSCHLAND GMBH, Bad Homburg (DE)

(72) Inventors: Pascal Kopperschmidt, Dittelbrunn (DE); Andreas Maierhofer, Schweinfurt (DE); Alfred Gagel, Litzendorf (DE); Andreas Wupper, Buttelborn (DE); Ulrich Moissl, Karben (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 109 days.

(21) Appl. No.: 15/501,180

(22) PCT Filed: Jul. 20, 2015

(86) PCT No.: PCT/EP2015/066582
§ 371 (c)(1),
(2) Date: Feb. 2, 2017

(87) PCT Pub. No.: WO2016/020180
PCT Pub. Date: Feb. 11, 2016

(65) Prior Publication Data
US 2017/0224897 A1    Aug. 10, 2017

(30) Foreign Application Priority Data

Aug. 7, 2014   (DE) .................. 10 2014 011 699

(51) Int. Cl.
*A61M 1/16* (2006.01)
*A61M 1/34* (2006.01)

(52) U.S. Cl.
CPC ........ *A61M 1/1615* (2014.02); *A61M 1/1617* (2014.02); *A61M 1/341* (2014.02);
(Continued)

(58) Field of Classification Search
None
See application file for complete search history.

(56) References Cited

U.S. PATENT DOCUMENTS

| 5,100,554 A | 3/1992 | Polaschegg |
| 2010/0042035 A1 | 2/2010 | Moissl et al. |

(Continued)

FOREIGN PATENT DOCUMENTS

| DE | 102011102962 A1 | 11/2012 |
| EP | 2514449 A1 | 10/2012 |

(Continued)

OTHER PUBLICATIONS

International Search Report and Written Opinion issued in corresponding International Patent Application No. PCT/EP2015/066582 (with English translation of International Search Report) dated Oct. 9, 2015 (12 pages).

(Continued)

*Primary Examiner* — Bradley R Spies
(74) *Attorney, Agent, or Firm* — Kilyk & Bowersox, P.L.L.C.

(57) ABSTRACT

The invention relates to a method and to a device for determining an optimum dialysate flow $Q_{dopt}$ for an extracorporeal blood treatment and to a blood treatment device comprising a device 18 for determining an optimum dialysate flow $Qd_{opt}$. The optimum dialysate flow $Qd_{opt}$ is determined on the basis of a relationship describing the (Continued)

dependence of the clearance K on the dialysate flow $Q_d$. The device according to the invention comprises a measurement device 18B for measuring at least one value which is characteristic of the clearance K, a calculation and/or evaluation unit 18A of the device according to the invention being configured in such a way that the clearance K is determined on the basis of the at least one value which is characteristic of the clearance. The calculation and/or evaluation unit 18A is configured in such a way that the optimum dialysate flow $Q_{dopt}$ is determined from the relationship describing the dependence of the clearance K on the dialysate rate $Q_d$ on the basis of the measured clearance K, or the optimum dialysate flow $Q_{dopt}$ is determined from the measured clearance K.

8 Claims, 3 Drawing Sheets

(52) U.S. Cl.
CPC ... *A61M 1/3413* (2013.01); *A61M 2205/3334* (2013.01); *A61M 2205/70* (2013.01)

(56) References Cited

U.S. PATENT DOCUMENTS

| | | |
|---|---|---|
| 2010/0168925 A1 | 7/2010 | Hilgers et al. |
| 2012/0298581 A1 | 11/2012 | Wehmeyer et al. |
| 2013/0020237 A1* | 1/2013 | Wilt .................... A61M 1/1037 210/85 |
| 2013/0303964 A1 | 11/2013 | Kopperschmidt et al. |
| 2014/0248600 A1* | 9/2014 | Hertz .................. A61M 1/3643 435/2 |

FOREIGN PATENT DOCUMENTS

| | | |
|---|---|---|
| WO | 2007/140993 A1 | 12/2007 |
| WO | 2007140993 A1 | 12/2007 |
| WO | 2013167264 A1 | 11/2013 |

OTHER PUBLICATIONS

International Preliminary Report on Patentability for corresponding International Patent Application No. PCT/EP2015/066582, dated Feb. 7, 2017, with corresponding Form PCT/IB/338 and Written Opinion of the International Searching Authority (Form PCT/ISA/237) (7 pages total).

* cited by examiner

DEVICE AND METHOD FOR DETERMINING AN OPTIMUM DIALYSATE FLOW FOR AN EXTRACORPOREAL BLOOD TREATMENT WITH AN EXTRACORPOREAL BLOOD TREATMENT DEVICE

This application is a National Stage Application of PCT/EP2015/066582, filed Jul. 20, 2015, which claims priority to German Patent Application No. 10 2014 011 699.9, filed Aug. 7, 2014, which are incorporated in their entireties by reference herein.

The invention relates to a device for determining an optimum dialysate flow for an extracorporeal blood treatment using an extracorporeal blood treatment device which comprises a dialyser which is subdivided by a semipermeable membrane into a blood chamber, which is flowed through by blood at a predetermined blood flow, and a dialysate chamber, which is flowed through by dialysate at a predetermined dialysate flow. The invention further relates to a blood treatment device comprising a device for determining an optimum dialysate flow and to a method for determining an optimum dialysate flow for an extracorporeal blood treatment using an extracorporeal blood treatment device. The invention relates to all methods of blood purification treatment in which blood flows through the blood chamber and dialysate flows through the dialysate chamber of a dialyser or filter, in particular haemodialysis or haemodiafiltration.

Various physical and/or chemical values are known by means of which the performance of a dialyser and/or the effectiveness of a dialysis treatment can be specified. One known value for specifying the effectiveness of a dialysis treatment is the clearance K. The clearance K of a substance is the sub-flow of the total flow through the dialyser which has been completely freed from the substance in question. What is known as the dialysis dose KT/V is of decisive importance for the effectiveness of a dialysis treatment, and is defined as the quotient of the product of the clearance K of urea and effective treatment time T of the dialysis treatment and the volume of distribution V of urea of the patient.

Methods and devices for measuring clearance during an extracorporeal blood treatment are known from DE 39 38 662 A1 (U.S. Pat. No. 5,100,554) and DE 197 47 360 A1 (U.S. Pat. No. 6,156,002). The clearance determination is based on measuring the electrolyte transfer at two different dialysate ion concentrations. From these documents, it is known that the clearance is dependent on the dialysate flow. The clearance is also dependent on the blood flow, although technically speaking only the effective blood water flow (plasma water and intracellular water) is decisive. A low blood water flow limits the clearance irrespective of a much higher dialysate flow. If the dialysate flow is less than the blood water flow, the dialysate flow limits the clearance. For simplicity, no distinction is made between blood water flow and blood flow in the following.

The known dialysis apparatuses make it possible to set different dialysate rates manually, for example 300, 500 and 800 ml/min. As a basic principle, to achieve a high clearance, higher dialysate flows are required at higher blood flows.

When a particular dialysate flow is set, it should be noted that although a high clearance can potentially be achieved using a high dialysate flow, the costs of providing fresh dialysate and disposing of used dialysate are increased. Therefore, in practice, a relatively high clearance is aimed for along with a relatively low consumption of dialysate.

U.S. Pat. No. 5,092,836 proposes to control the dialysate flow as a function of the blood flow in accordance with predetermined criteria. It is in particular proposed to set a dialysate flow which is provided by multiplying the blood flow by a constant factor. As well as a linear relationship between blood and dialysate flows, a numerical data field is proposed which specifies, for each blood flow of a particular dialyser, the dialysate flow which achieves a particular percentage of the maximum clearance which would be present assuming an infinitely high dialysate flow.

DE 10 2006 045 437 A1 (U.S. 2010/042035A1) discloses a device for determining an optimum dialysate flow on the basis of a relationship describing the dependence of the clearance on the dialysate flow. The determination of the optimum dialysate flow is based on determining, for a predetermined blood flow, the dialysate flow for which, when it is increased by a particular value, the increase in the clearance is not less than a particular value. However, the optimum dialysate flow is also dependent on the dialyser which is used for the dialysis treatment. Therefore, DE 10 2006 045 437 A1 provides that a value which is characteristic of the dialyser, in particular the mass transfer coefficient, is taken into account. The mass transfer coefficient is a parameter of the dialyser provided by the dialyser manufacturer, which should be inputted to determine the optimum dialysate flow by the known method. DE 10 2006 045 437 A1 provides that different mass transfer coefficients are taken into account for different types of dialysers.

An object of the invention is to specify a device and a method for determining an optimum dialysate flow for an extracorporeal blood treatment using an extracorporeal blood treatment device whilst taking into account the dialyser used for the blood treatment, in view of the need both for high effectiveness of the dialysis treatment and for a low dialysate consumption. A further object of the invention is to provide a blood treatment device by means of which dialysis treatment of relatively high effectiveness can be carried out at a relatively low dialysate flow. Another object of the invention is to specify a method for determining an optimum dialysate flow so as to be able to carry out a dialysis treatment of a relatively high effectiveness at a reasonable dialysate consumption.

This object is achieved according to the invention by the features of the dependent claims. The dependent claims relate to advantageous embodiments of the invention.

The device according to the invention for determining an optimum dialysate flow has a calculation and/or evaluation unit which is configured in such a way that the optimum dialysate rate for the dialyser of the blood treatment device is determined from a relationship describing the dependence of the clearance on the dialysate flow.

In this connection, a calculation and/or evaluation unit is understood to be any unit which receives and/or evaluates signals or data and/or generates or supplies signals or data. The calculation and/or evaluation unit may be a central unit or comprise a plurality of separate components. It may for example be a data processing unit (microprocessor) having a storage unit on which a data processing program (software) runs.

The invention has two aspects which are of inventive significance independently of one another. However, both aspects are based on measuring the clearance before or during the blood treatment to determine the optimum dialysate flow.

The device according to the invention comprises a measuring device for measuring at least one value which is characteristic of the clearance, the calculation and/or evaluation unit being configured in such a way that the clearance can be determined on the basis of the at least one value which is characteristic of the clearance.

The calculation and/or evaluation unit of the device according to the invention is configured in such a way that the optimum dialysate flow is determined from the relationship describing the dependence of the clearance on the dialysate flow on the basis of the measured clearance. When the clearance which occurs at a particular dialysate flow is known, the characteristic parameter of the respectively used dialyser can be determined, in particular the mass transfer coefficient of the dialyser, which has an effect on the efficiency of the blood treatment. As a result, the mass transfer coefficient provided by the manufacturer does not have to be used. For the device according to the invention and the method according to the invention, it is thus not necessary to know a parameter of this type of the dialyser used.

It has been found that measuring the clearance, instead of using a parameter of the dialyser provided by the manufacturer, to determine the optimum dialysate flow on the basis of the relationship between the dialysate flow and the clearance has the advantage that changes in the properties of the dialyser during the blood treatment as a result of blocking of the membrane (clotting) can also be included. Further, the optimum dialysate flow can be determined precisely even if the mass transfer coefficient provided by the manufacturer does not characterise the dialyser well enough, for example as a result of manufacturing tolerances.

The invention is based on the fact that, for different dialysers having different parameters or for a dialyser of which the parameter varies, the dependence of the clearance on the dialysate flow is always described by a characteristic curve. In the case of different dialysers or varying dialyser properties, there is therefore a set of curves.

The first aspect of the invention involves using the measured clearance to select the relevant curve, which is used to determine an optimum working point, from the set of curves.

A preferred embodiment of the invention provides the mass transfer coefficient of the dialyser as the parameter thereof. The calculation and/or evaluation unit is preferably configured in such a way that the mass transfer coefficient $K_oA$ of the dialyser is calculated using the following equation in the case of haemodialysis (HD):

$$K_OA = \frac{Q_b \cdot Q_d}{Q_b - Q_d} \ln\left(\frac{Q_d(Q_b - K)}{Q_b(Q_d - K)}\right), \quad \text{equation (1)}$$

Qd being the dialysate flow, Qb being the blood (water) flow and K being the measured clearance.

Once the mass transfer coefficient $K_oA$ has been calculated on the basis of the clearance measurement before or during the blood treatment, the relationship describing the dependence of the clearance on the dialysate flow, in other words the characteristic curve for establishing the optimum working point, is determined. The calculation and/or evaluation unit is preferably configured in such a way that the relationship describing the dependence of the clearance on the dialysate rate for the case of haemodialysis (HD) is determined on the basis of the following equation:

$$K = Q_b \frac{e^{K_0 A \left(\frac{1}{Q_b} - \frac{1}{Q_d}\right)} - 1}{e^{K_0 A \left(\frac{1}{Q_b} - \frac{1}{Q_d}\right)} - \frac{Q_b}{Q_d}}, \quad \text{equation (2)}$$

$Q_d$ being the dialysate flow, $Q_b$ being the blood (water) flow and $K_oA$ being the mass transfer coefficient of the dialyser.

For determining the optimum working point on the characteristic curve, a preferred embodiment provides that the calculation and/or evaluation unit is configured in such a way that, on the basis of the relationship describing the dependence of the clearance on the dialysate flow at a predetermined blood flow rate $Q_b$, the dialysate flow $Q_d$ is determined for which, when it is increased by a particular value, the increase in the clearance is not less than a particular value.

The device according to the invention and the method according to the invention thus assume that, from an optimum value for the dialysate flow at a particular blood flow rate upwards, although a further increase in the effectiveness of the dialysis treatment can be achieved by further increasing the dialysate rate, the additional dialysate required for a more effective treatment of this type is not in an economic ratio to the associated increase in effectiveness. Thus, as a target criterion, the working point is sought at which the additional dialysate consumption which would be required to increase the clearance by a particular value is not greater than a particular value. This method is disclosed in DE 10 2006 045 437 A1, to which reference is hereby explicitly made.

The device according to the invention may be a separate means or a component of the blood treatment device. Therefore, the calculation and/or evaluation unit may also be a separate unit or part of the central control or calculation or evaluation unit of the blood treatment device.

Another aspect of the invention involves establishing the optimum working point on the characteristic curve by a preferably iterative method to determine the optimum dialysate flow on the basis of at least one clearance measurement.

In a preferred embodiment, the calculation and/or evaluation unit is configured in such a way that the difference between the value of the clearance measured at a predetermined dialysate flow and a predetermined value for the clearance is calculated, a control signal for decreasing the dialysate flow by a predetermined amount being generated if the difference between the measured clearance and the predetermined clearance is positive, and a control signal for increasing the dialysate flow by a predetermined amount being generated if the difference between the measured clearance and the predetermined clearance is negative.

The clearance can be predetermined freely by the doctor with a view to the aim of the treatment, taking into account the possible treatment parameters. The clearance may correspond to a value which is to be achieved by the blood treatment in all cases. It may also correspond to a value which is not to be exceeded, in particular in patients who are undergoing a dialysis treatment for the first time. The control signals are used to intervene in the machine control of the blood treatment device so as to set the respective flow rates.

The amount by which the dialysate flow is decreased or increased is preferably an amount dependent on the magnitude of the difference between the measured or calculated and predetermined clearances. The greater the deviation, the greater the change in the dialysate flow should be.

In a particularly preferred embodiment, the clearance measurement, the calculation of the difference between the measured and predetermined clearances, and the generation of a control signal for increasing or decreasing the dialysate flow preferably take place in a plurality of successive steps, in such a way that the optimum working point is determined in an iterative process. To avoid constant flow alterations, it may be provided that the dialysate flow is only increased or decreased until the magnitude of the difference between the currently measured clearance and the predetermined clearance reaches or undershoots a predetermined threshold.

The device according to the invention and the method according to the invention can be used to give the doctor carrying out the dialysis treatment a suggestion for setting an optimum dialysate flow. It is further preferred that the predetermined dialysate rate is not only suggested to the doctor carrying out the treatment, but is actually automatically set for the blood treatment.

An alternative preferred embodiment provides for successively increasing or decreasing or maintaining the dialysate flow as a function of whether a predetermined criterion is met. In the preferred embodiment, the dialysate flow is successively increased as long as a particular criterion is met; for example, it is checked whether the increase from the preceding value to the following value has led to an increase in the clearance which is in a particular ratio to the increase in the dialysate flow.

In the following, various embodiments of the invention are described in greater detail with reference to the drawings, in which.

Figure 1:
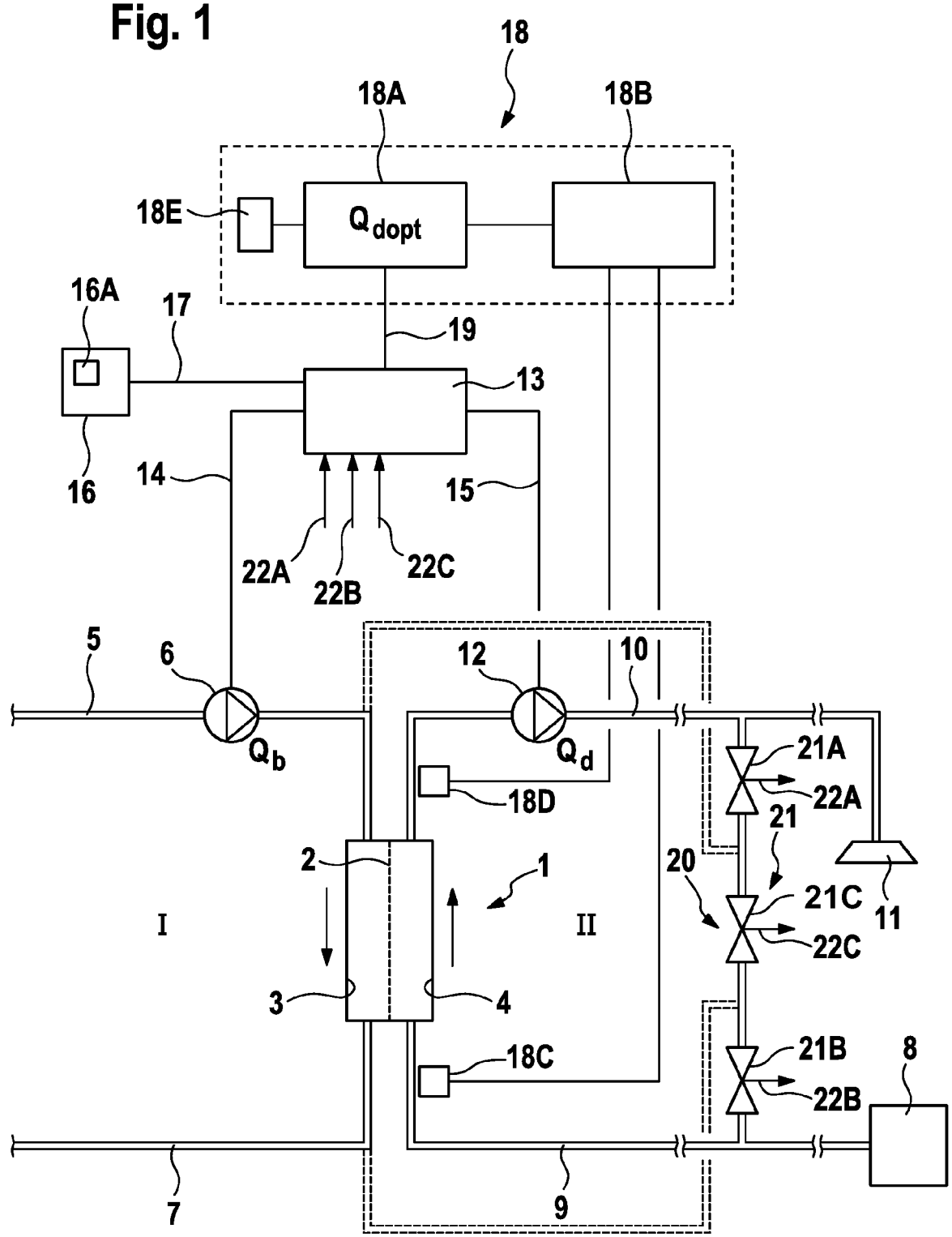
FIG. 1 is a highly schematic drawing of the essential components of a device according to the invention for extracorporeal blood treatment using a device according to the invention for predetermining an optimum dialysate flow.

FIG. 1 shows an embodiment of a blood treatment device according to the invention which has a device 18 according to the invention for determining an optimum dialysate flow $Qd_{opt}$. For improved clarity, FIG. 1 merely shows the essential components of the blood treatment device, since the individual components of a blood treatment device for haemodialysis or haemodiafiltration are generally known to the person skilled in the art.

The dialysis device according to the invention has a dialyser 1, which is subdivided by a semipermeable membrane 2 into a blood chamber 3 and a dialysate chamber 4. An arterial blood line 5, into which a blood pump 6 is connected, leads from a patient to an inlet of the blood chamber 3, whilst a venous blood line 7 leads from an outlet of the blood chamber 3 of the dialyser 1 to the patient. During the blood treatment, the arterial and venous blood lines 5, 7 of the extracorporeal blood circuit I are connected to the patient via cannulas (not shown).

Fresh dialysate is provided in a dialysate source 8. A dialysate supply line 9 leads from the dialysate source 8 to an inlet of the dialysate chamber 4, whilst a dialysate removal line 10 leads from an outlet of the dialysate chamber 4 of the dialyser 1 to a drain 11. A dialysate pump 12 is connected into the dialysate removal line 10.

The dialysate system II of the dialysis device comprises further components, of which only a bypass line 20 comprising a valve arrangement 21 is shown in FIG. 1, however. One end of the bypass line 20 is connected to the dialysate supply line 9 upstream from the dialysate chamber 4 and the other end of the bypass line 20 is connected to the dialysate removal line 10 downstream from the dialysate chamber. The valve arrangement 21 comprises two outer valves 21A and 21B and a central valve 21C, which are arranged in the bypass line.

The dialysis device has a central control unit 13, which is connected to the blood pump 6 and the dialysate pump 12 via control lines 14, 15. The control unit 13 generates control signals for operating the blood and dialysate pump 6, 12 at a predetermined feed rate, in such a way that a predetermined blood flow $Q_b$ is established in the blood line 5, 7 and a predetermined dialysate flow $Q_d$ is established in the dialysate line 9, 10. The valves 21A, 21B, 21C are electromagnetically actuatable valves, which are connected to the control unit 13 via control lines 22A, 22B, 22C.

To input different parameters for the dialysis, the dialysis device has an input unit 16, which comprises for example an alphanumeric keypad 16A. The input unit 16 is connected via a data line 17 to the control unit 13, by means of which the individual components of the dialysis device are actuated in such a way that the dialysis treatment is carried out using the predetermined dialysis parameters.

The dialysis device provides an optimum dialysate flow $Q_{dopt}$ for the dialysis treatment. For this purpose, the dialysis device has a device 18 for determining an optimum dialysate flow $Q_{dopt}$, the construction and operation of which are disclosed in detail in the following.

The dialysis treatment is carried out using a particular dialyser 1 which has a particular effectiveness. The effectiveness of the dialyser 1 is specified by way of the mass transfer coefficient $k_0A$, although this does not have to be known to determine the optimum dialysate flow $Q_{dopt}$.

In the case of haemodialysis (HD), the clearance K is calculated from the blood (water) flow $Q_b$ and the dialysate flow $Q_d$ and the mass transfer coefficient $k_0A$ of the dialyser 1 using the following equation:

$$K = Q_b \frac{e^{K_0 A \left(\frac{1}{Q_b} - \frac{1}{Q_d}\right)} - 1}{e^{K_0 A \left(\frac{1}{Q_b} - \frac{1}{Q_d}\right)} - \frac{Q_b}{Q_d}}. \tag{2}$$

Figure 2:
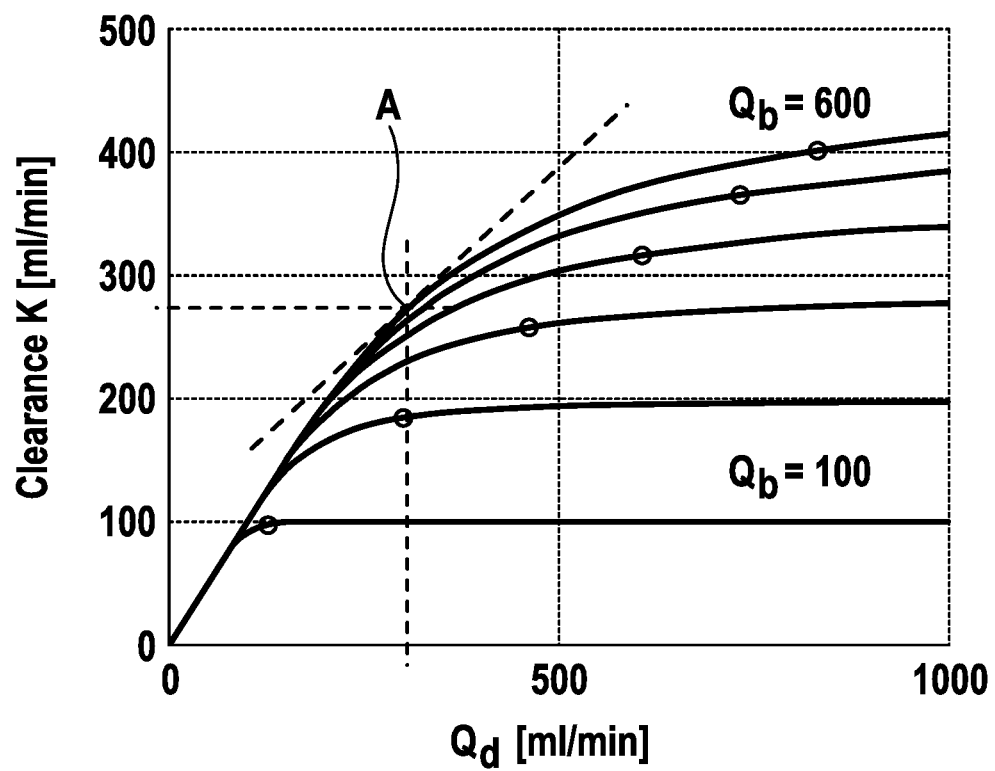
FIG. 2 shows the clearance K (ml/Min) as a function of the dialysate flow $Q_d$ (ml/min) for various blood flow rates $Q_b$.

FIG. 2 shows the clearance K as a function of the dialysate flow $Q_d$ for various blood flows $Q_b$. It can be seen that at high dialysate flows $Q_d$ the clearance K is saturated. Therefore, from a particular dialysate flow $Q_{dopt}$ upwards, increasing the dialysate flow does not lead to a significant gain in clearance. If the gain in clearance is negligible, a change in the dialysate rate can be omitted or a decrease in the dialysate flow may be expedient. By contrast, if the change in the dialysate rate leads to a significant increase in the clearance, the dialysate rate should be increased. Using a critical value crit, it can be established whether the dialysate flow should be decreased or increased or can be left unchanged.

$$dK(Q_d)/dQ_d < \text{crit}_1 \qquad \text{equation (3.1)}$$

$Q_d$ is decreased $$\text{crit}_1 < dK(Q_d)/dQ_d < \text{crit}_2 \qquad \text{equation (3.2)}$$

$Q_d$ is *not* changed $$dK(Q_d)/dQ_d < \mathrm{crit}_2 \qquad \text{equation (3.3)}$$

$Q_d$ is increased

The device 18 for determining the optimum dialysate flow $Q_{dopt}$ has a calculation and/or evaluation unit 18A, which is connected to the central control unit 13 of the blood treatment device via a line 19 in such a way that the calculation and/or evaluation unit 18A and control unit 13 can receive and transmit control signals or data.

Further, the device for determining the optimum dialysate flow $Q_{dopt}$ has a measurement device 18B for measuring a value which is characteristic of the clearance, in particular the dialysate ion concentration at the input and output of the dialysate chamber of the dialyser. To measure the dialysate input concentration and the dialysate output concentration, the measurement device 18B comprises a conductivity sensor 18C on the dialysate supply line 9 upstream from the dialysate chamber 2 and a conductivity sensor 18D on the dialysate removal line 10 downstream from the dialysate chamber 2 of the dialyser 1, which are merely alluded to in FIG. 1. The measurement of the clearance K is based on the electrolyte concentration being briefly raised or lowered, the conductivity of the dialysate being measured upstream and downstream from the dialysate chamber 2 using the sensors 18C, 18D before the change in the electrolyte concentration. The calculation and/or evaluation unit can calculate the clearance from the dialysate input concentrations $c_{di}(1)$ and $c_{di}(2)$ and dialysate output concentrations $c_{do}(1)$ and $c_{do}(2)$ using the following equation:

$$K = Q_d(((c_{di}(1)-c_{do}(1))-(c_{di}(2)-c_{do}(2)))/(c_{di}(1)-c_{di}(2)) \qquad \text{equation (4)}$$

Measurement devices of this type are known for example from DE 39 38 662 A1 (U.S. Pat. No. 5,100,554) and DE 197 47 360 A1 (U.S. Pat. No. 6,156,002), to which reference is hereby explicitly made. However, it is irrelevant to the invention how the clearance is calculated from the measured values.

The device 18 according to the invention predetermines an optimum dialysate flow $Q_{dopt}$, at which the dialysis device is operated. It is assumed that a particular blood flow $Q_b$ is set, which can be inputted at the input unit 16. For this purpose, the calculation and/or evaluation unit 18A is configured as follows.

The clearance K is initially measured at the set blood flow $Q_b$ for a predetermined dialysate flow $Q_d$. Using equation (4), the calculation and/or evaluation unit 18A calculates the clearance K from the measured conductivity values before and after the change in the electrolyte concentration. Once the clearance K is known, in the case of haemodialysis (HD) the calculation and evaluation unit 18A calculates the mass transfer coefficient $k_0A$ of the dialyser 1 using equation (1):

$$K_OA = \frac{Q_b \cdot Q_d}{Q_b - Q_d} \ln\left(\frac{Q_d(Q_b - K)}{Q_b(Q_d - K)}\right),$$

$Q_d$ being the dialysate flow, $Q_b$ being the blood (water) flow and K being the previously measured clearance.

Since the mass transfer coefficient $k_0A$ of the dialyser 1 is determined using the clearance measurement in advance of determining the optimum working point, this parameter of the dialyser does not have to be known. The dialyser parameter can be determined before or during the dialysis treatment. The parameter can be determined at particular time intervals during the dialysis treatment, in such a way that changes in the mass transfer coefficient which are attributable to blocking of the membrane (clotting) can also be taken into account.

Using a clearance measurement, the mass transfer coefficient does not have to be determined during the blood treatment, but can also be determined in advance of the blood treatment during a rinsing process.

To rinse the blood chamber of the dialyser, the arterial blood lines 5 is connected to the portion of the bypass line 20 between one outer valve 21A and the inner valve 21C, and the venous blood line 7 is connected to the portion of the bypass line 20 between the other outer valve 21B and the inner valve 21C, and in the bypass line 20 the outer valves 21A and 21B are opened and the middle valve 21C is closed by the control unit 13. The blood lines 5, 7 connected to the bypass line 20 for the rinsing process are shown in dashed lines in FIG. 1. During the rinsing process, a rinsing liquid, in particular a dialysate, is supplied to the blood chamber 3 via the dialysate supply line 9 and the portion of the venous blood line 7 and removed from the blood chamber via the portion of the venous blood line 5 and the dialysate removal line 10. When the rinsing process is complete, the control unit 13 closes the outer valves 21A, 21B and opens the central valve 21C in the bypass line 20, the blood pump 6 being operated in such a way that the rinsing liquid recirculates through the blood chamber 3. At the same time, the dialysate pump 12 is operated in such a way that dialysate flows into the dialysate chamber 4 and out of the dialysate chamber 4.

The clearance is subsequently determined by the above-described known methods, rinsing liquid, in particular a dialysate, flowing through the blood chamber instead of blood. For this purpose, the electrolyte concentration of the dialysate flowing into the dialysate chamber 4 is briefly changed, and the response to the concentration bolus is measured in the dialysate flowing out of the dialysate chamber 4. The measurements may also be taken upstream and downstream from the dialyser, for which purpose the conductivity sensors 18C and 18D may be used. From the flow rate for the rinsing liquid, which corresponds to the blood flow rate $Q_b$ in a measurement during the blood treatment, and the dialysate flow rate $Q_d$, along with the measured conductivity values, the calculation and/or evaluation unit 18A calculates the mass transfer coefficient using equation (1). This can be determined for different dialysers and hose line systems. However, when the mass transfer coefficient is calculated using equation (1), it should be taken into account that equation (1) does not precisely describe the actual ratios because of the lower volume of liquid flowing through the blood chamber by comparison with the measurement during the blood treatment and because of the recirculation of the liquid. The calculation and/or evaluation unit 18A therefore makes a correction to the calculated value using an empirically determined correction factor, which takes into account the filling volume of the blood chamber and of the hose line system. This correction factor can be determined by laboratory experiments and stored in a memory of the calculation and/or evaluation unit 18A.

Once the mass transfer coefficient $k_0A$ is known, in the case of haemodialysis (HD) the calculation and/or evaluation unit 18A calculates the relationship between the clearance K and the dialysate flow $Q_b$ using equation (2):

$$K = Q_b \frac{e^{K_0 A \left(\frac{1}{Q_b} - \frac{1}{Q_d}\right)} - 1}{e^{K_0 A \left(\frac{1}{Q_b} - \frac{1}{Q_d}\right)} - \frac{Q_b}{Q_d}},$$

$Q_d$ being the dialysate flow, $Q_b$ being the blood (water) flow and $K_o A$ being the mass transfer coefficient of the dialyser.

The calculation and/or evaluation unit 18A can calculate the clearance K for different dialysate flows Qd using equation (1) so as subsequently to find the optimum working point for the dialysis device, as is disclosed in DE 10 2006 045 437 A1.

The optimum working points for different blood flow rates are marked by circles in FIG. 2, a ratio of additional dialysate flow [ml/min] and additional clearance [ml/min] of 10:1 having been selected for the working points. If the dialysate rate $Q_d$ is increased further starting from the respective working point, an increase in the dialysate rate is no longer associated with a further increase in clearance K which exceeds a particular value. The optimum dialysate rate $Q_{dopt}$ is therefore the dialysate flow for which, when it is exceeded, the derivative of the function shown in FIG. 2, which describes the dependence of the clearance K on the dialysate rate $Q_d$, undershoots a particular critical value. A possible but non-optimum working point is denoted A in FIG. 2.

The clearance measurement in advance of determining the optimum working point makes it superfluous to determine a three-dimensional curve family, by means of which the optimum dialysate flow rate $Q_{dopt}$ can be determined as a function of the blood flow rate $Q_b$ for different dialysers which are each distinguished by a particular mass transfer coefficient K0A.

To display the optimum dialysate flow $Q_{dopt}$, the device 18 has a display unit 18E, for example in the form of a screen or a display.

Further, the device 18 outputs the calculated value for the optimum dialysate flow $Q_{dopt}$ via the line 19 to the control unit 13 of the blood treatment device, which in turn sets the rotational speed of the dialysate pump 12 in such a way that dialysate is conveyed at the optimum dialysate flow $Q_{dopt}$.

Another aspect of the invention likewise provides measurement of the clearance to determine an optimal dialysate rate.

At the input unit 16 for the blood treatment, the doctor can predetermine a particular clearance $K_{min}$ which should not be undershot during the blood treatment. However, he can also predetermine a value for the clearance $K_{max}$ which should not be exceeded. The clearance $K_m$ is measured at a predetermined dialysate flow $Q_d$.

Once the actual clearance $K_m$ is known, the calculation and/or evaluation unit 18A calculates the difference between the measured clearance $K_m$ and the predetermined for example minimum clearance $K_{min}$. If the difference is positive, the calculation and/or evaluation unit 18A generates a control signal, in such a way that the control unit 13 of the blood treatment device decreases the dialysate flow $Q_d$. By contrast, if the difference is negative, the calculation and/or evaluation unit generates a control signal for the control unit to increase the dialysate flow $Q_d$. The amount $\Delta Q_d$ by which the dialysate flow $Q_d$ is decreased or increased is proportional to the magnitude of the difference between the measured clearance $K_m$ and the minimum clearance $K_{min}$. A large difference thus leads to a large change in the dialysis rate, for example by 20%. Preferably, the dependence is a linear function. The difference $K_m - K_{min}$ can also be based on $K_{min}$ (for example $(K_m - K_{min})/K_{min} \times 100\% > 20\%$).

After the change in the dialysate flow $Q_d$, a clearance measurement is taken again so as to be able to establish whether the aim of the treatment is still being achieved. The calculation and/or evaluation unit 18A calculates the difference between the measured clearance $K_m$ and the minimum clearance $K_{min}$. If the difference is still positive, the dialysate flow $Q_d$ is decreased again in a further step. By contrast, if the difference is negative the dialysate flow is increased.

The optimum dialysate flow $Q_{dopt}$ can be determined in a plurality of iterative steps, the dialysate rate being changed by a particular amount, which is proportional to the magnitude of the difference between the measured clearance $K_m$ and the minimum clearance $K_{min}$, in each step. To avoid constant flow rate changes, the calculation and/or evaluation unit 18A compares the difference between the measured clearance $K_m$ and the minimum clearance $K_{min}$ with a predetermined threshold, which may for example be between 2% and 5% of the minimum clearance $K_{min}$. If the threshold is achieved or undershot, the calculation and/or evaluation unit 18A interrupts the iterative process, the currently set dialysate flow $Q_d$ being accepted as the optimum dialysate flow $Q_{dopt}$.

Figure 3:
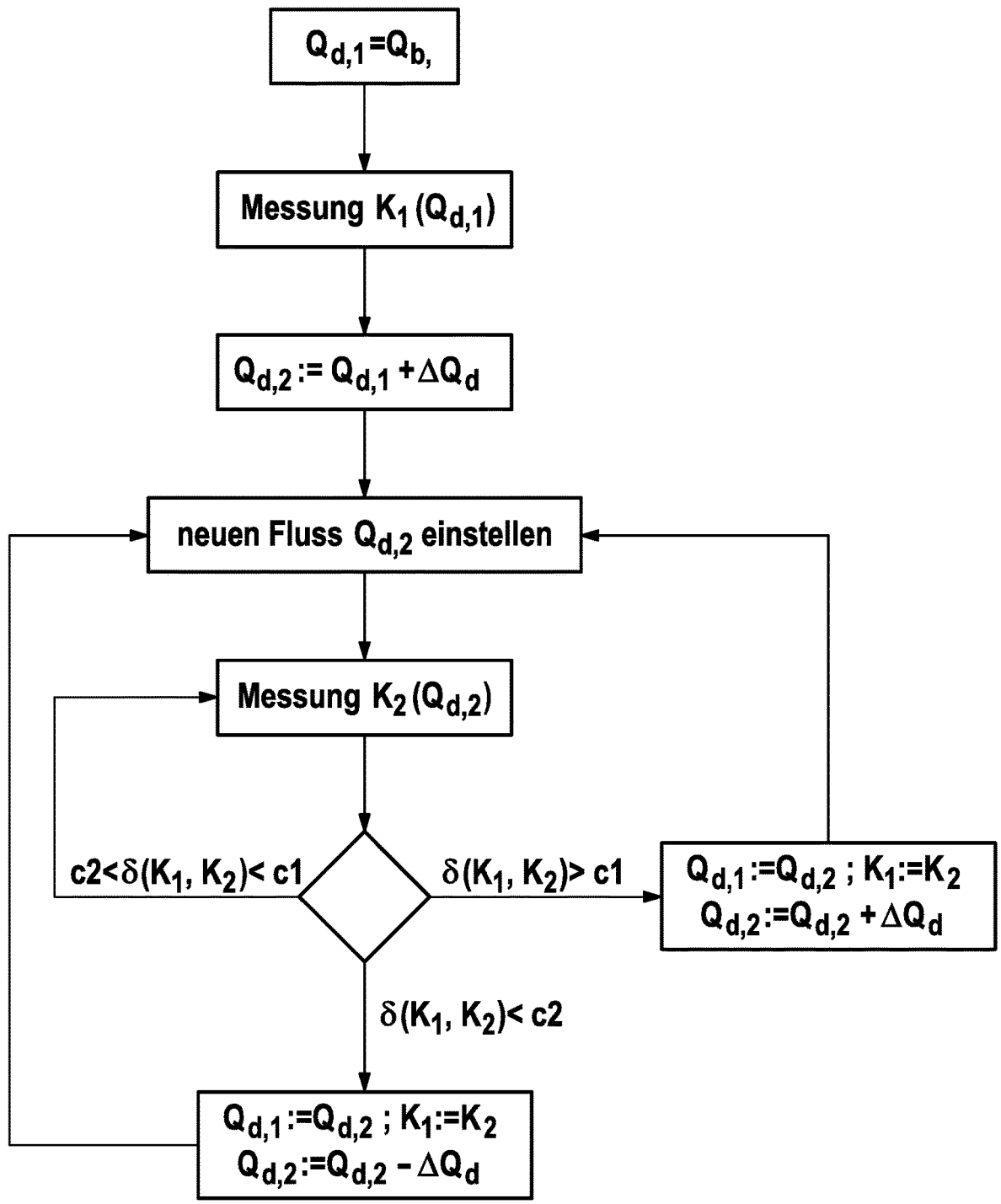
FIG. 3 is a flow diagram comprising the method steps for determining an optimum dialysate flow $Qd_{opt}$ by an iterative method.

A further embodiment of the invention for determining the optimum dialysate flow $Q_{dopt}$ by an iterative method which is based on measuring the clearance K is disclosed in the following. The individual method steps, which may be carried out at the start of or in the course of the blood treatment, are shown in FIG. 3.

The control unit 13 initially generates a control signal, which predetermines a dialysate flow $Q_{d,1}$ corresponding to the blood flow $Q_b$. The clearance $K_1$ is measured at the predetermined blood flow $Q_b$ and dialysate flow $Q_{d,1}$, it again being possible to determine the clearance by the above-disclosed method. The control unit subsequently increases the dialysate flow $Q_{d,1}$, by the amount $\Delta Q_d$, for example by 50 ml/min, to $Q_{d,2}$. Subsequently, the clearance is measured again at the blood flow $Q_b$ with result $K_2$. The two measurements are subsequently evaluated by the calculation and/or evaluation unit 18A as follows.

From the data tuples $[K_1, Q_{d,1}]$ and $[K_2, Q_{d,2}]$, the calculation and/or evaluation unit 18A calculates the relative change in the clearance of $K_1$ and $K_2$ as a result of the change in the dialysate flow by $\Delta Q_{d12}$ from $Q_{d,1}$ to $Q_{d,2}$, to and calculates the gradient $\Delta K_{12}/\Delta Q_{d12}$ of the relative change in the clearance $\Delta K_{12}$ and in the relative dialysate flow $\Delta Q_{d12}$:

$$\Delta K_{12}/\Delta Q_{d12} = (K2 - K1)/(Q_{d,2} - Q_{d,1}) \qquad \text{equation (5)}$$

The change in the clearance of $K_1$ and $K_2$ as a result of the change in the dialysate flow by $\Delta Q_{d12}$ from $Q_{d,1}$ to $Q_{d,2}$ is checked by the calculation and/or evaluation unit 18A as to whether a criterion is met for increasing or decreasing or maintaining the dialysate flow $Q_d$. For this purpose, the calculation and/or evaluation unit compares the gradient $\Delta K_{12}/\Delta Q_{d12}$ of the relative change in the clearance and in the relative dialysate flow with a first threshold $c_1$ and a second threshold $c_2$, the first threshold being greater than the second threshold. However, the second threshold may also be equal to the first threshold.

If the gradient $\Delta K_{12}/\Delta Q_{d12}$ is greater than the first threshold $c_1$, the calculation and control unit 13 generates a control signal to increase the dialysate flow $Q_d$, in such a way that the dialysate flow $Q_d$ is further increased by $\Delta Q_d$.

If the gradient $\Delta K_{12}/\Delta Q_{d12}$ is less than the second threshold $c_2$, the calculation and control unit 13 generates a control signal to decrease the dialysate flow $Q_d$, in such a way that the dialysate flow $Q_d$ is decreased by $\Delta Q_d$ again.

If the gradient $\Delta K_{12}/\Delta Q_{d12}$ is less than the first threshold $c_1$ and greater than the second threshold $c_2$, a control signal to maintain the dialysate flow $Q_d$ is generated, in such a way that the optimum dialysate flow $Q_{dopt}$ is determined and is also set.

If the gradient $\Delta K_{12}/\Delta Q_{d12}$ is greater than the first threshold $c_1$ or less than the second threshold $c_2$, after the increase or decrease in the dialysate flow the clearance K is measured again, so as to be able to check again the change in the clearance from the previously measured value to the current value as a result of the increase or decrease in the dialysate flow for whether the above criterion is met. This process is continued until the gradient $\Delta K_{12}/\Delta Q_{d12}$ is less than the first threshold and greater than the second threshold and the dialysate flow is no longer being changed.

The device according to the invention and the method according to the invention aim to optimise the dialysate flow on the basis of the determination of the diffusive component of the dialyser clearance. The device according to the invention and the method according to the invention can be used for determining an optimum dialysate flow not only for haemodialysis (HD), but also for haemodiafiltration (HDF). In the case of haemodiafiltration (HDF), the following values occur:

$K_oA$: diffusive mass transfer coefficient or coefficient of diffusive mass transfer, which takes into account the diffusive component of the dialyser clearance;

$Q_d$: dialysate flow through the dialyser, which is to be distinguished from the total flow of the dialysate $Q_{d,tot}$, which is the sum ($Q_{d,tot}=Q_d+Q_s$) of the dialysate flow $Q_d$ through the dialyser and the substituate flow $Q_s$;

$Q_{d,opt}$ optimum dialysate flow;

$Q_{bw}$: blood water flow at the arterial cannula. The blood flow at the dialyser input is increased by supplying substituate upstream from the dialyser (pre-dilution), whilst the blood flow at the dialyser output is decreased by ultrafiltration and by supplying substituate downstream from the dialyser (post-dilution). The blood water flow $Q_{bw}$ is dependent on the haematocrit and the protein content in the blood, $Q_{bw}$ being approximately 0.86 $Q_b$;

$K_{m,tot}$: measured system clearance, which comprises the total purification power of the system including the convective and diffusive component of the clearance, patient effects which decrease the clearance, for example recirculation, being taken into account;

$K_{m,diff}$: diffusive component of the system clearance, which is derived from the measured system clearance $K_{m,tot}$ and is based on the calculation of the diffusive mass transfer coefficient $K_oA$.

The clearance calculated to determine the optimum dialysate flow $Q_{d,opt}$ is dependent on the dialysate flow $Q_d$ and the blood flow $Q_b$, and is denoted as $K_d(Q_d, Q_b, K_oA)$.

There is a difference between haemolysis (HD) and haemodiafiltration (HDF) in particular in the case of haemodiafiltration with pre-dilution (HDF pre-dilution), since the blood-side liquid flow is composed of the blood flow and the substituate flow. The diffusive exchange in the dialyser thus takes place for the total flow:

$$K_{m,diff} = \frac{Q_{bw} + \kappa Q_s}{Q_b - Q_f - (1-\kappa)Q_s}\left(\frac{Q_{bw} + \kappa Q_s}{Q_b}K_m - Q_f - Q_s\right),$$

$\kappa=1$ for HDF pre-dilution $\kappa=0$ for HD and HDF post-dilution

For HDF post-dilution, this relationship is simplified to $$K_{m,diff} = \frac{Q_b}{Q_b - Q_f - Q_s}(K_m - Q_f - Q_s)$$

Instead of equation (1), in the case of haemodiafiltration (HDF) this gives:

$$k_0A = \frac{(Q_b + \kappa Q_s)Q_d}{Q_d - Q_b - \kappa Q_s}\ln\left(\frac{\frac{K_{m,diff}}{Q_d} - 1}{\frac{K_{m,diff}}{Q_b + \kappa Q_s} - 1}\right) \quad \text{equation (1')}$$

which, in the case of haemodialysis or HDF post-dilution where $\kappa=0$, gives:

$$k_0A = \frac{Q_bQ_d}{Q_d - Q_b}\ln\left(\frac{\frac{K_{m,diff}}{Q_d} - 1}{\frac{K_{m,diff}}{Q_b} - 1}\right)$$

For the general case of haemodiafiltration (HDF), the relationship describing the dependence of the clearance $K_d$ on the dialysate flow $Q_d$ is as follows:

$$K_d = (Q_{bw} + \kappa Q_s)\frac{e^\gamma - 1}{e^\gamma - \frac{(Q_{bw} + \kappa Q_s)}{Q_d}}, \quad \text{equation (2')}$$

$$\gamma = k_0A\frac{Q_d - (Q_{bw} + \kappa Q_s)}{(Q_{bw} + \kappa Q_s)Q_d}$$

For HD and HDF post-dilution ($\kappa=0$), this relationship is again simplified to:

$$K_d = Q_{bw}\frac{e^\gamma - 1}{e^\gamma - \frac{Q_{bw}}{Q_d}}, \quad \gamma = k_0A\frac{Q_d - Q_{bw}}{Q_{bw}Q_d}$$

From the dialysate input concentrations $c_{di}(1)$ and $c_{di}(2)$ and dialysate output concentrations $c_{do}(1)$ and $c_{do}(2)$, the clearance can be calculated using the following equation.

Instead of using equation (4), for the general case of haemodiafiltration, the calculation and/or evaluation unit 18A calculates the clearance as follows once the dialysate input concentrations $c_{di}(1)$ and $c_{di}(2)$ and dialysate output concentrations $c_{do}(1)$ and $c_{do}(2)$ have been measured:

$$K_{m,tot} = (Q_d + Q_f + Q_s)\left(1 - \frac{c_{do}(2) - c_{do}(1)}{c_{di}(2) - c_{di}(1)}\right) \quad \text{equation (4')}$$

$Q_f$ being the total filtration rate, in other words the total of the ultrafiltration rate $Q_{UF}$ and the substituate rate $Q_S$.

When the dialysate input concentrations $c_{di}(1)$ and $c_{di}(2)$ and dialysate output concentrations $c_{do}(1)$ and $c_{do}(2)$ are varied continuously (pulse profile) rather than incrementally (stepped profile), the clearance is calculated as follows:

$$K_{m,tot} = (Q_d + Q_s + Q_f)\left(1 - \frac{\int_{t_2}^{t_3} \Delta c_{do}(t')dt'}{\int_{t_0}^{t_1} \Delta c_{di}(t')dt'}\right)$$

$\Delta_{cj}$ being the height of the LF variation above the base line.

The above equations apply when blood and dialysate flow in a counter flow in the dialyser. If by contrast blood and dialysate flow in a parallel flow in the dialyser, the following relationships apply for the general case of haemodiafiltration (Gotch, Replacement of Renal Function).

$$k_0 A = \frac{Q_b Q_d}{Q_d + Q_b} \ln\left(\frac{Q_b}{Q_b - K_d\left(1 + \frac{Q_b}{Q_d}\right)}\right)$$

$$k_0 A = -\frac{Q_b Q_d}{Q_d + Q_b} \ln\left(1 - K_d\left(\frac{1}{Q_b} + \frac{1}{Q_d}\right)\right)$$

$$K_d = Q_{bw} \frac{1 - e^{-\gamma}}{1 + \frac{Q_{bw}}{Q_d}}, \gamma = k_0 A \frac{Q_d + Q_{bw}}{Q_{bw} Q_d}.$$

The invention claimed is:

1. A method for determining an optimum dialysate flow rate, $Q_{dopt}$, into a dialysate chamber of a dialyser during an extracorporeal blood treatment using an extracorporeal blood treatment device comprising the dialyser, the dialyser being subdivided by a semipermeable membrane into the dialysate chamber and a blood chamber, the method comprising:

rinsing the blood chamber of the dialyser with dialysate and measuring clearance K of the dialyser prior to flowing blood through the blood chamber, to obtain a measured clearance value K, calculating a mass transfer coefficient from the measured clearance value K via an equation that relates the mass transfer coefficient to clearance, thereby obtaining a calculated mass transfer coefficient $k_o A$, after said rinsing, flowing blood through the blood chamber of the dialyser at a predetermined blood flow rate $Q_b$, and after said rinsing, flowing dialysate through the dialysate chamber of the dialyser at a predetermined dialysate flow rate $Q_d$, wherein said rinsing occurs while dialysate is flowing through a dialysate circuit and through the dialysate chamber, which is part of said dialysate circuit, wherein said rinsing comprises: i) opening a first valve that is in fluid communication with a dialysate supply line of the dialysate circuit, the first valve connected to a venous line of a blood circuit via a first line, said venous line being connected to the blood chamber of the dialyser; ii) opening a second valve that is in fluid communication with a dialysate return line of the dialysate circuit, the second valve being connected to an arterial line of a blood circuit via a second line, said arterial line being connected to the dialyser; iii) closing a third valve that connects to the first valve and the second valve via a line connecting the first valve to the third valve and a line connecting the second valve to the third valve; and iv) operating a blood pump, located in the blood circuit, in such a way that the dialysate recirculates through the blood chamber of the dialyser by flowing dialysate from the dialysate supply line, through the first valve, through the first line, through the venous line, through the blood chamber, through the arterial line, through the second line, through the second valve, and to the dialysate return line, thereby accomplishing said rinsing, wherein said measuring clearance K during said rinsing is carried out by measuring a change in electrolyte concentration of the dialysate in the dialysate circuit and flowing the dialysate through the dialysate chamber during said rinsing, and wherein, upon obtaining the calculated mass transfer coefficient $k_o A$, the optimum dialysate flow rate $Q_{dopt}$ is determined from a relationship describing the dependence of clearance K on the predetermined dialysate flow rate $Q_d$.

2. The method according to claim 1, wherein the relationship describing the dependence of the clearance K on the predetermined dialysate flow rate $Q_d$ is determined on the basis of the following equation:

$$K = Q_b \frac{e^{K_0 A\left(\frac{1}{Q_b} - \frac{1}{Q_d}\right)} - 1}{e^{K_0 A\left(\frac{1}{Q_b} - \frac{1}{Q_d}\right)} - \frac{Q_b}{Q_d}},$$

$Q_d$ being the dialysate flow rate, $Q_b$ being the blood (water) flow rate, and $K_o A$ being the mass transfer coefficient of the dialyser.

3. The method according to claim 1, wherein the mass transfer coefficient $K_o A$ of the dialyser is calculated using the following equation:

$$K_O A = \frac{Q_b \cdot Q_d}{Q_b - Q_d} \ln\left(\frac{Q_d(Q_b - K)}{Q_b(Q_d - K)}\right),$$

$Q_d$ being the dialysis flow rate, $Q_b$ being the blood (water) flow rate, and K being the measured clearance.

4. The method according to claim 1, wherein, on the basis of the relationship describing the dependence of the clearance K on the predetermined dialysate flow rate $Q_d$ at the predetermined blood flow rate $Q_b$, the optimum dialysate flow rate $Q_{dopt}$ is determined for which, when it is increased by a particular value, the increase in the clearance is not less than a particular value.

5. The method according to claim 1, further comprising a first step and a second step, wherein, in the first step a clearance $K_m$ is measured at the predetermined dialysate flow rate $Q_d$, wherein the predetermined dialysate flow rate $Q_d$ is increased by a predetermined amount, wherein, in the second step, the clearance $K_m$ is measured at the predetermined dialysate flow rate $Q_d$ increased by the predetermined amount, wherein the change in the clearance $K_m$ as a result of the change in the dialysate flow rate is checked as to whether a criterion is met for increasing or decreasing or maintaining the predetermined dialysate flow rate $Q_d$, the predetermined dialysate flow rate $Q_d$ being increased if the criterion for increasing the predetermined dialysate flow rate $Q_d$ is met, the predetermined dialysate flow rate $Q_d$ being decreased if the criterion for decreasing the predetermined dialysate flow rate $Q_d$ is met, the predetermined dialysate flow rate $Q_d$ being maintained if the criterion for maintaining the predetermined dialysate flow rate $Q_d$ is met, and wherein, if the criterion for increasing or decreasing the predetermined dialysate flow rate $Q_d$ is met in successive steps, the predetermined dialysate flow rate $Q_d$ is increased or decreased to an adjusted flow rate and the change in the clearance $K_m$ as a result of the change in the dialysate flow rate is checked as to whether the criterion is met for increasing or decreasing or maintaining the adjusted flow rate until the criterion for maintaining the predetermined dialysate flow rate $Q_d$ is met.

6. The method according to claim 5, wherein a gradient of a relative change in the clearance $K_m$ for a relative change in the predetermined dialysate flow rate $Q_d$ is calculated as the criterion for increasing or decreasing or maintaining the predetermined dialysate flow rate $Q_d$, wherein the predetermined dialysate flow rate $Q_d$ is increased if the gradient of the relative change in the clearance $K_m$ for the relative change in the predetermined dialysate flow rate $Q_d$ is greater than a first threshold, wherein the predetermined dialysate flow rate $Q_d$ is decreased if the gradient of the relative change in the clearance $K_m$ for the relative change in the predetermined dialysate flow rate $Q_d$ is less than a second threshold, and wherein the predetermined dialysate flow rate $Q_d$ is maintained if the gradient of the relative change in the clearance $K_m$ for the relative change in the predetermined dialysate flow rate $Q_d$ is less than the first threshold and greater than the second threshold.

7. The method according to claim 1, wherein, to measure the clearance K, a flow connection is established between the arterial blood line and the venous blood line, and the dialysate is recirculated through the blood chamber, wherein an electrolyte concentration of a liquid flowing into the dialysate chamber is changed upstream from the dialyser, and wherein an electrolyte concentration of liquid flowing out of the dialysate chamber is measured.

8. The method according to claim 1, wherein the electrolyte concentration of the dialysate flowing into the dialysate chamber is briefly changed, and the response to the change is measured in the dialysate flowing out of the dialysate chamber.

* * * * *